United States Patent [19]
Buddingh

[11] Patent Number: 5,086,759
[45] Date of Patent: Feb. 11, 1992

[54] CHIROPRACTIC BELT

[76] Inventor: C. Curtis Buddingh, 22114 Ventura Blvd., Woodland Hills, Calif. 91364

[21] Appl. No.: 507,373

[22] Filed: Apr. 10, 1990

[51] Int. Cl.⁵ ............................ A61F 5/02; A61F 5/24
[52] U.S. Cl. .................................. 602/19; 128/101.1; 128/96.1; 272/143
[58] Field of Search ............... 128/24 R, 78, 95.1, 128/96.1, 99.1, 100.1, 101.1, 68; 272/143

[56] References Cited

U.S. PATENT DOCUMENTS

| | | | |
|---|---|---|---|
| 261,494 | 7/1882 | Teufel | 128/96.1 |
| 1,995,002 | 3/1935 | Lee | 128/78 |
| 2,100,964 | 11/1937 | Kendrick | 128/78 |
| 2,104,699 | 1/1938 | O'Dell | 128/78 |
| 2,117,309 | 5/1938 | Fritsch | 128/78 |
| 2,219,475 | 10/1940 | Flaherty | 128/78 |
| 2,409,381 | 10/1946 | Pease, Jr. | 128/78 X |
| 2,476,029 | 7/1949 | Dawson | 128/78 X |
| 2,554,337 | 5/1951 | Lampert | 128/78 X |
| 3,096,760 | 7/1963 | Nelkin | 128/78 X |
| 3,097,640 | 7/1963 | Morgan | 128/78 |
| 3,441,027 | 4/1969 | Lehman | 128/78 X |
| 3,545,446 | 12/1970 | Nobbs | 128/78 X |
| 3,561,434 | 2/1971 | Kilbey | 128/78 X |
| 3,926,183 | 12/1975 | Spiro | 128/78 |
| 3,927,665 | 12/1975 | Wax | 128/78 |
| 4,099,524 | 7/1978 | Cueman et al. | 128/78 |
| 4,245,628 | 1/1981 | Eichler | 128/78 |
| 4,685,668 | 8/1987 | Newlin, Jr. | 272/143 X |
| 4,794,916 | 1/1989 | Porterfield et al. | 128/101.1 X |
| 4,884,562 | 12/1989 | Stone | 128/78 |
| 4,964,401 | 10/1990 | Taigen | 272/123 |

Primary Examiner—Robert Bahr
Assistant Examiner—Linda C. M. Dvorak
Attorney, Agent, or Firm—Plante, Strauss, Vanderburgh & Connors

[57] ABSTRACT

Disclosed is a chiropractic belt 10 having two belt segments 16 and 18 joined together by a central elastic section 12. There is an elastic cross-structure 26 which overlies and is connected at the intersection of the cross-structure to the mid-section of the elastic member. The ends of the cross-structure are connected to the belt segments. Right hand and left hand tensioning members 58 and 60 are attached at the midsection at the intersection of the cross structure, with free ends of the tensioning members being adapted to be connected or disconnected, respectively, to the left and right hand belt segments.

7 Claims, 5 Drawing Sheets

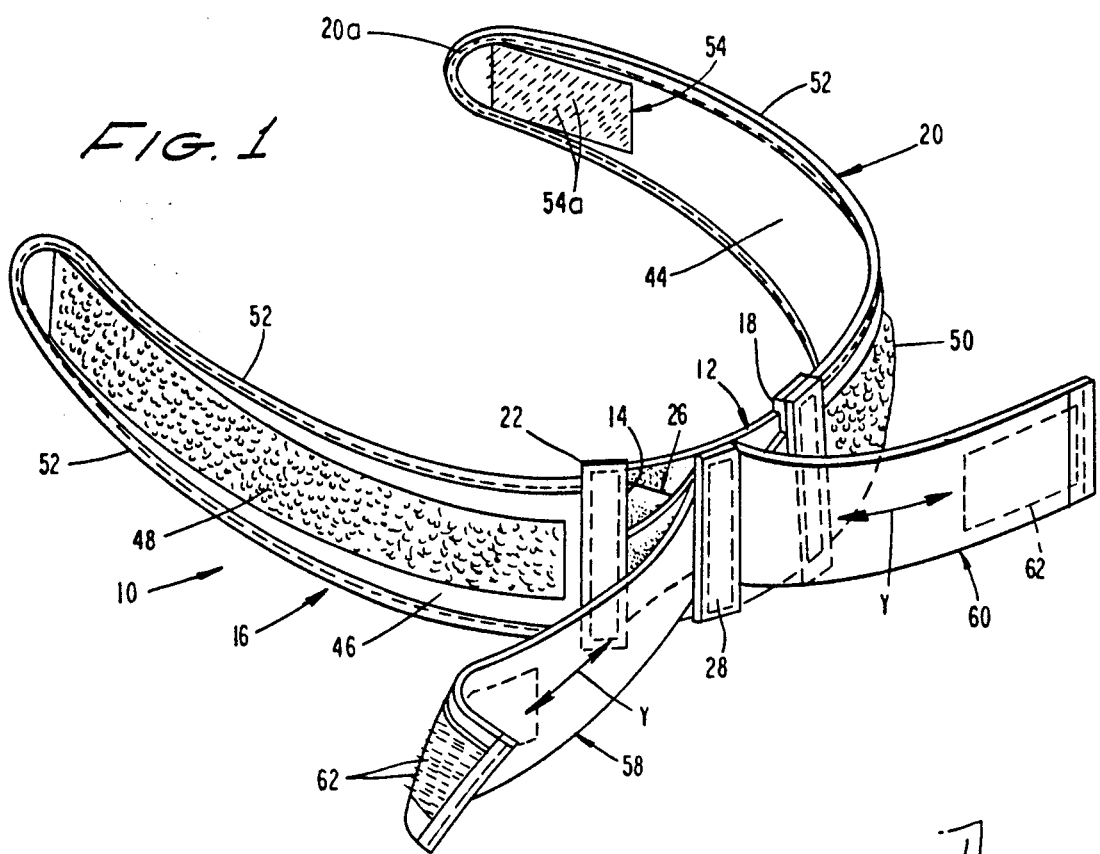
FIG. 1
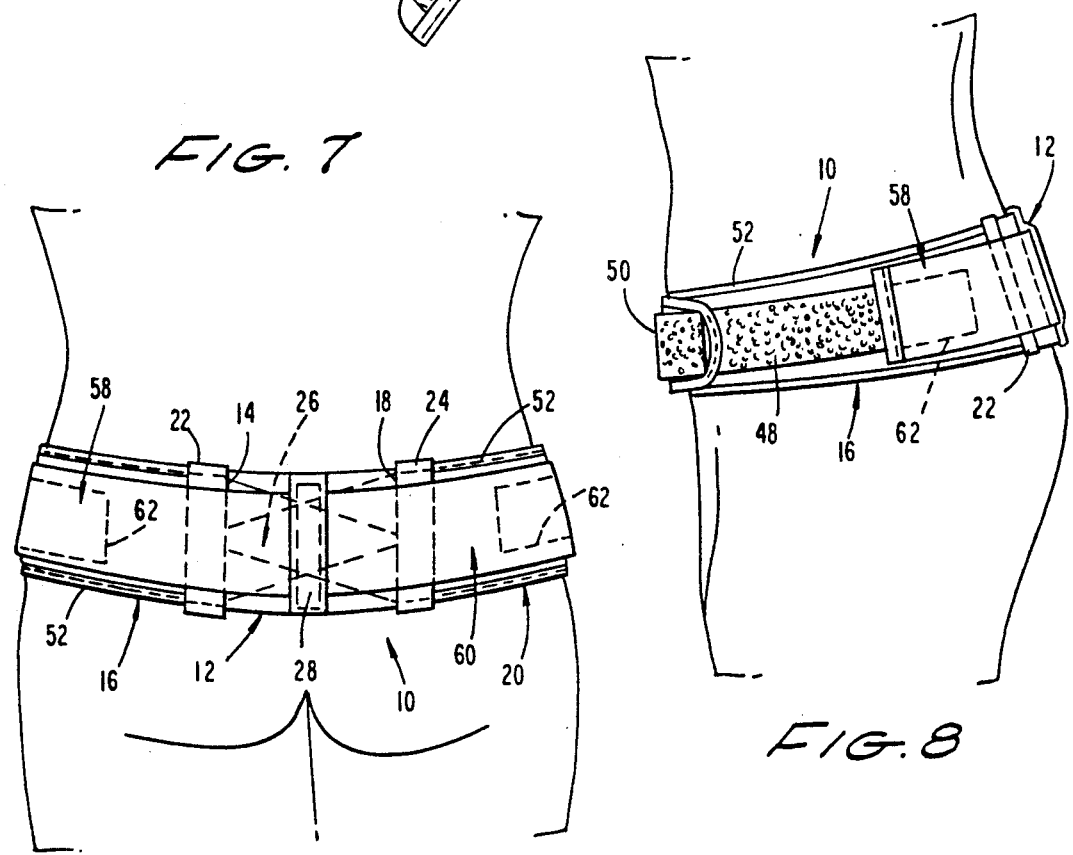
FIG. 7
FIG. 8

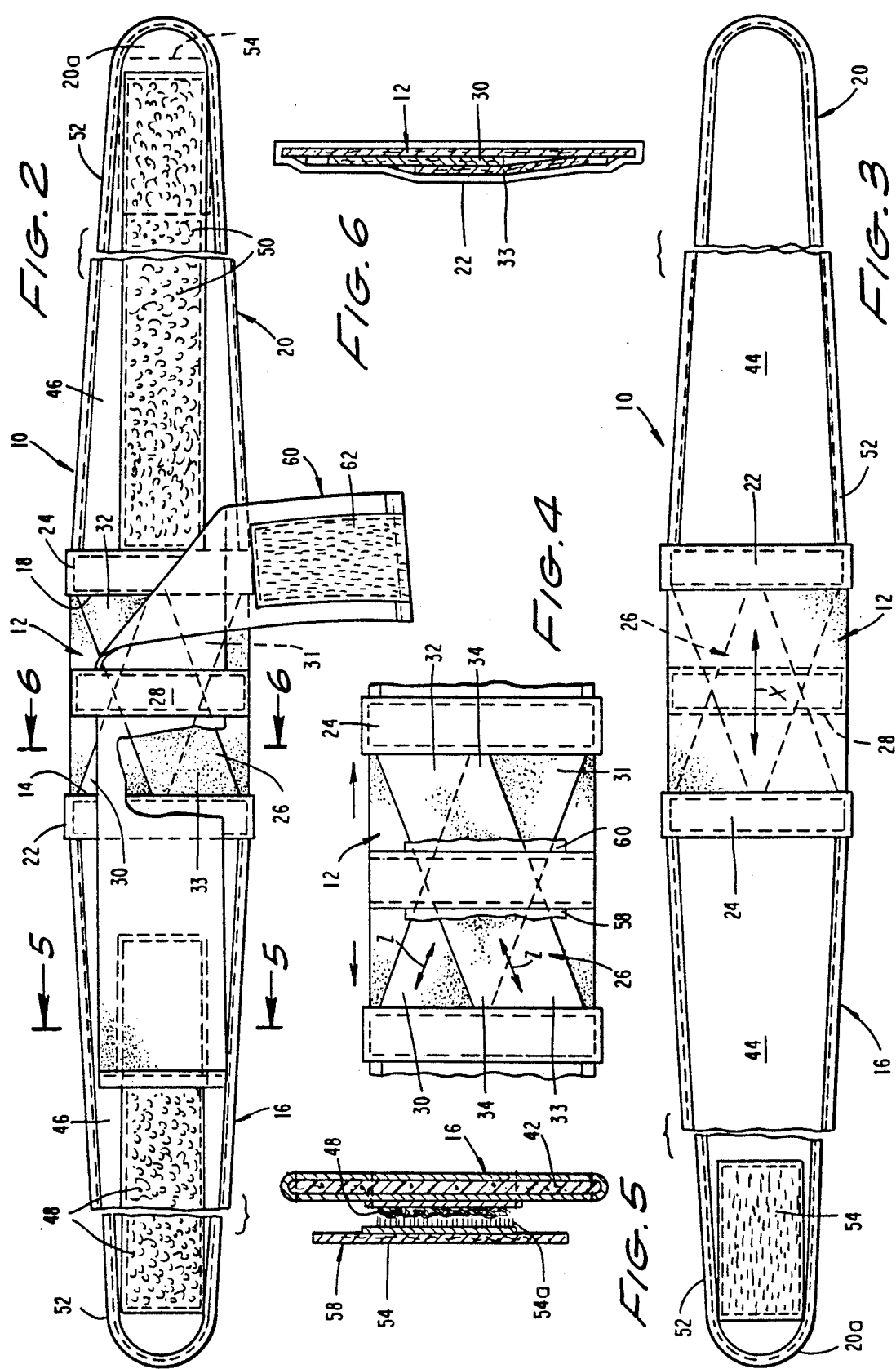

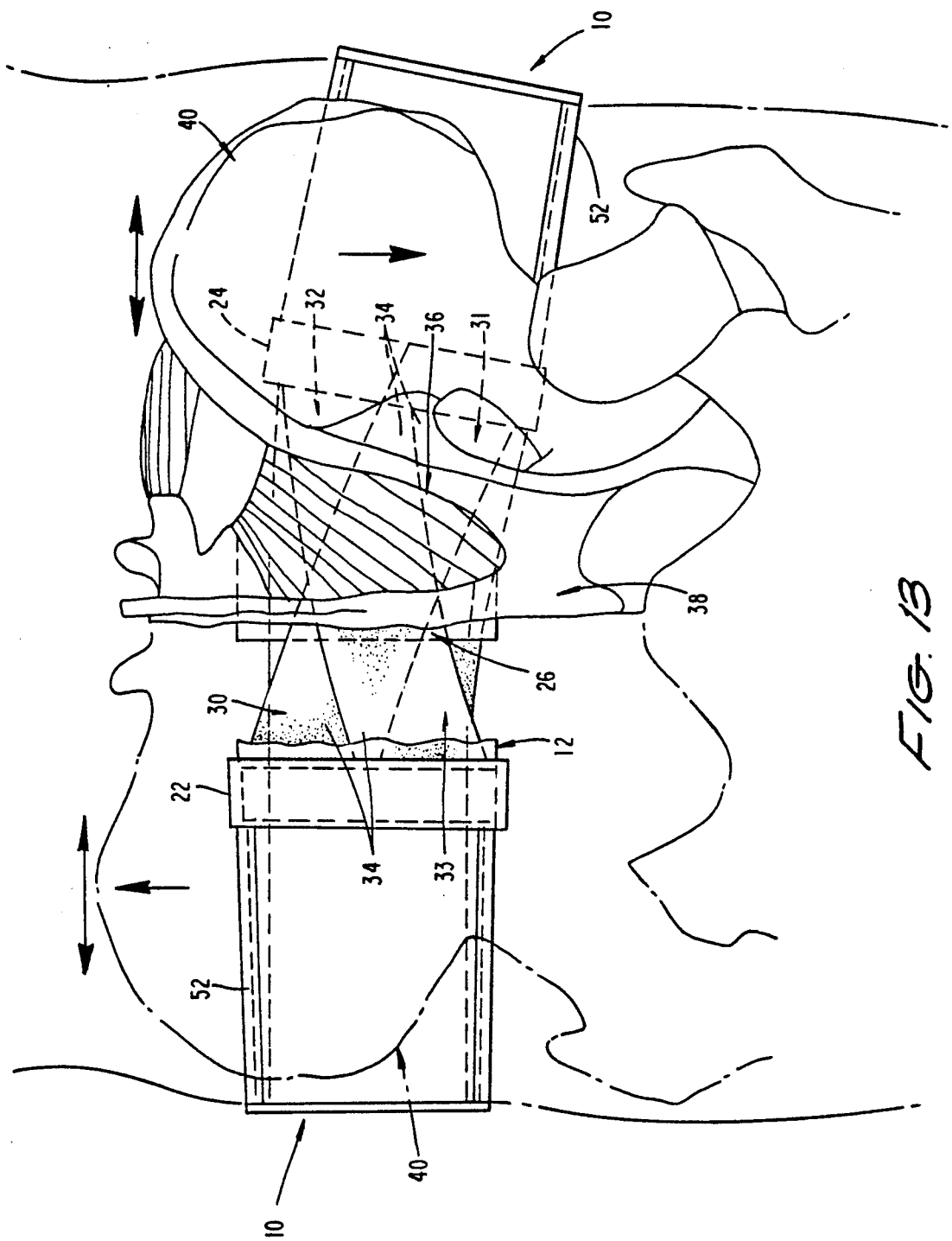

CHIROPRACTIC BELT

BACKGROUND OF THE INVENTION

1. Field of the Invention

This invention relates to a chiropractic belt for relieving the pain, discomfort, and instability resulting from ligament and other connective tissue sprain and strain in the lower back of a person. This belt also enhances and sustains chiropractic adjustments and reduces the probability of injury when correctly worn during physical activity. Particularly, this invention relates to a chiropractic belt which allows a complete range of movement of the pelvic region of the user without unnecessary restriction of muscle movement, thereby avoiding or lessening atrophy.

2. Background Discussion

During normal activity, lifting a heavy object, or vigorous or repetitive body motion, a person's muscles in the lower back may be sprained, strained, or both. When a ligament is stressed beyond its elastic limit, the injured person's sacrum and the ilium (bones in the pelvic region) separate beyond their normal relationship, creating a neuromuscular instability. Excess synovia fluid fills the gap between the sacrum and ilium. Consequently, the stretched ligaments which normally hold the sacrum and ilium closely adjacent remain in an elongated condition because of the presence of the excess synovia fluid.

A common practice is to immobilize the pelvic lumbar region, at least to a limited extent, in order to allow the torn or stretched ligaments and other connective tissue to heal. Sometimes orthopedic belts have been employed to limit the normal movement in the pelvic region. The belt compresses the sacrum and ilium, squeezing the excess synovia fluid from the gap, and brings these bones into correct alignment. This allows for the ligaments and other connective tissue to stabilize and heal. The problem with this type of procedure is that the normal range of pelvic movement of the person is restricted and the muscles atrophy. This prolongs the period of pain, discomfort, and recovery. If the conventional orthopedic belt remains in position for a very long time, muscle and connective tissue damage can occur. What makes matters even more problematic is that the onset of muscle and connective tissue atrophication occurs within hours after restricting the normal range of movement in the pelvic region.

SUMMARY OF THE INVENTION

The chiropractic belt of this invention has several features, no single one of which is solely responsible for its desirable attributes. Without limiting the scope of this invention as expressed by the claims which follow, its more prominent features will now be discussed briefly. After considering this discussion, and particularly after reading the section of this application entitled, "DETAILED DESCRIPTION OF THE PREFERRED EMBODIMENT," one will understand how the features of this invention provide its advantages such as comfort, speed of recovery, and effective therapy for back pain.

The first feature of this invention is that the belt includes a central elastic member which, when the belt is worn around the pelvic region of a user and correctly positioned on the user's body, generally overlies the sacroiliac region of the body of the user. This central elastic member has a width corresponding to the normal width of the sacroiliac region, or about four and one. half to about five and one-half inches, and a height corresponding to the height of the sacroiliac region, or about three and one-half to about four and one half inches. Preferably, the elastic member is a conventional knitted elastic cloth-like material made from polyester and rubber or Lycra filaments. Typically the filaments have a gage ranging from about 26 to about 34. This material should have the capability to elongate approximately from about 75 to about 300 percent of its original length. The elongation occurs in only one axis of orientation, the horizontal axis when the belt is worn by a user in a standing position.

The second feature of this invention is that there is a cross structure made of a flexible elastic material overlying the central elastic member. Preferably, this cross-structure is made of two elastic cloth members having a width of approximately one half inch to three inches, preferably one and one half to two inches. These two members crisscross to intersect, with the intersection overlying the midsection of the central elastic member. The cross-structure is secured to the midsection of the central elastic member, providing four outwardly extending elastic arms. These arms have a length ranging from 1.5 to 3.0 inches. The outer ends of the arms are secured respectively to left and right hand belt segments. These belt segments are attached, respectively, to the left and right hand sides of the central elastic member.

The four arms are grouped in pairs that work together. The two arms of each pair are in tandem alignment with each other, with one being above the other when the belt is correctly worn. The right upper arm of one pair is generally in parallel alignment with the right hand posterior sacro-iliac ligaments which connect the sacrum of the user to the ilium of the user. The left upper arm of the other pair is generally in parallel alignment with the left hand posterior sacro-iliac ligaments which connect the sacrum of the user to the ilium of the user.

The third feature of this invention is the use of tension adjusting members which enable the user to increase or decrease the amount of tension applied by the belt to the user's pelvic region. Each tension adjusting member is a flexible elastic strip which has one end connected to the midsection of the central elastic member and a free end which may be connected or disconnected to one of the belt segments. Specifically, there is a right hand adjusting member that is detachably secured to the right hand belt segment and a left hand adjusting member that is detachably secured to the left hand belt segment.

DESCRIPTION OF THE DRAWING

The preferred embodiment of this invention illustrating all its features will now be discussed in detail. This embodiment depicts the novel and non-obvious chiropractic belt of this invention. The drawing accompanying this application, which is for illustrative purposes only, includes the following figures, with like numerals indicating like parts:

FIG. 1 is a perspective view of the chiropractic belt of this invention.

FIG. 2 is a plan view, with sections broken away, of the exterior side of the chiropractic belt of this invention.

FIG. 3 is a plan view of the interior side of the chiropractic belt of this invention.

FIG. 4 is a fragmentary view of the central section in an expanded condition of the chiropractic belt of this invention.

FIG. 5 is a cross-sectional view taken along line 5—5 of FIG. 2.

FIG. 6 is a cross-sectional view taken along line 6—6 of FIG. 2.

FIG. 7 is a rear view of a person wearing the chiropractic belt of this invention.

FIG. 8 is a side view of a person wearing the chiropractic belt of this invention.

FIG. 13 is a schematic view of the posterior of a human skeleton showing the elongation of the central section of chiropractic belt of this invention as the sacrum and ilium of the user move during exercise.

DESCRIPTION OF THE PREFERRED EMBODIMENT OF THE INVENTION

Figure 9:
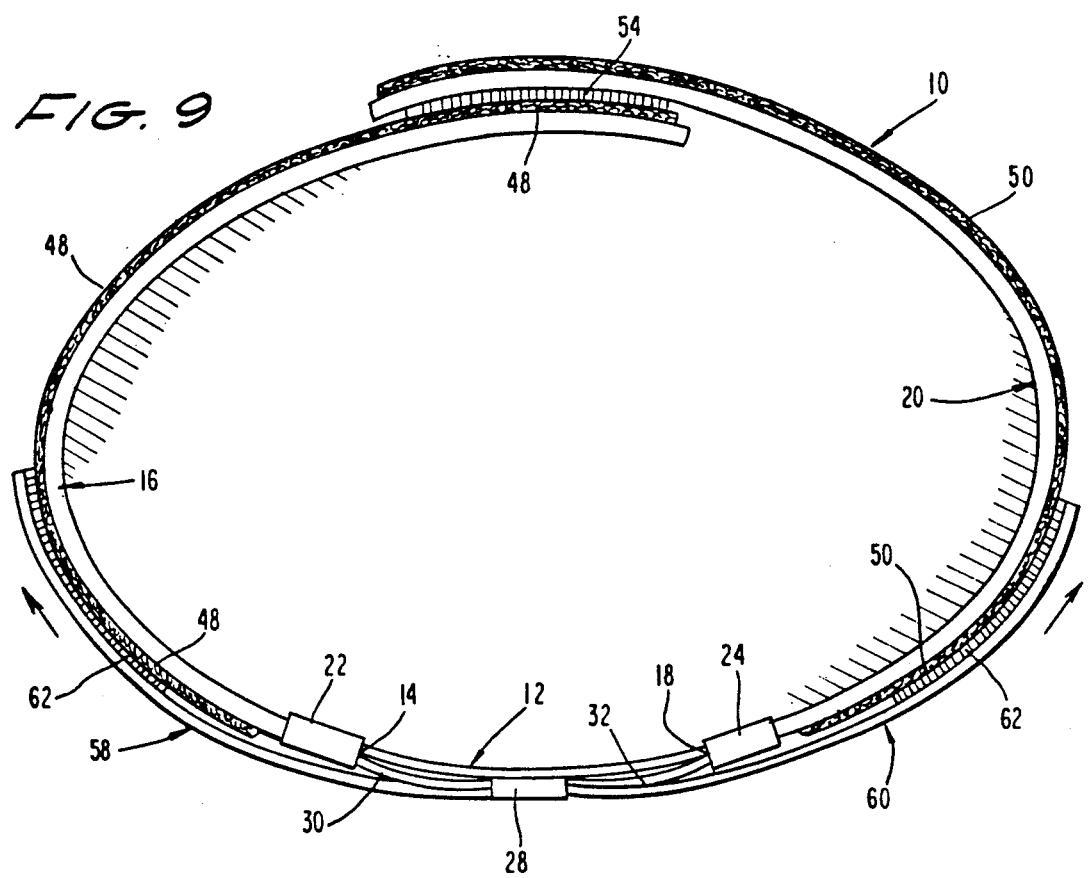
FIG. 9 is a plan view looking downward at the top edge of the chiropractic belt of this invention, with the belt being wrapped around the pelvic region of a user.

As best illustrated in FIGS. 1, 2, 3, 4, 12 and 13, the chiropractic belt 10 of this invention includes a generally rectangular elastic central section 12. This central section 12 has a width of approximately five inches and a height of approximately four inches. It can be stretched lengthwise along the longitudinal axis X (FIG. 3). A suitable elastic fabric material for use as the central section 12 may be purchased from Mianna, Inc. of Sun Valley, California. The percent elongation of this material normally ranges between 75 and 300 percent. The left hand edge 14 of the central elastic member 12 is secured, for example, by sewing, to a flexible left hand belt segment 16. The right hand edge 18 of the central elastic section 12 has a right hand belt segment 20 secured to it, for example, by sewing. There are left and right hand reinforcing strips 22 and 24 which, respectively, overlie the junctions between the left hand belt segment line of connection with the central elastic section 12 and the right hand belt segment line of connection with the central elastic member.

A cross-structure 26 overlies the exterior of the central elastic section 12 and is secured to the midsection of this section, for example, by sewing, preferably using a reinforcing strip 28 which intersects the center of the cross-structure. The cross-structure 26 has four, outwardly extending arms 30-33, each approximately two inches in width and each approximately two inches in length. These arms 30-33 may be formed from the same material as the central section 12, and essentially only elongate along their longitudinal axes Z. For example, two four inch strips of this material may be placed over each other in a criss-cross fashion and then sewn in position. The extremities 34 (FIG. 4) of these arms 30-33 are overlying or near each other, depending upon the width of the arms. When the belt 10 is correctly worn, the point of overlap or adjacency of the extremities 34 of the arms 30-33 is aligned with the fulcrum 36 (FIG. 13) where the sacrum 38 and ilium 40 pivot. This will be explained in greater detail subsequently.

Each of the belt segments 18 and 20 has an interior made of a thin layer 42 (FIG. 5) of foam. This foam layer 42 will conform over time with the contours of the body of the person wearing the belt. The inner surfaces 44 of the belt segments 18 and 20 are a woven cotton material and the exterior surfaces 46 are a tightly woven, durable cotton material. Each of the belt segments 18 and 20 have on their exterior surfaces 46 loop or pile members 48 and 50, respectively. A boarder 52 of durable cloth or other material is sewn around the edge of the belt segments 18 and 20 to resist wear, making the belt 10 more durable. The interior surface 46 at the end 20a of the right hand belt segment 20 has a rectangular hook structure 54, with the hooks 54a grasping the pile segment 48 when this end 20a is brought into an overlying relationship and pressed against the exterior of the pile member 48. Suitable hook and pile fasteners for use with the belt 10 are sold under the trademark Velcro. Such a Velcro-type fastener is the most desirable way of connecting the two belt segments 18 and 20 together, however, other suitable fastener means could also be used.

A pair of tension adjusting members 58 and 60 are secured to the exterior of the belt 10. Each tension adjusting member 58 and 60 has one end connected to the midsection of the central elastic section 12 and, at its other end, has a hook member 62 (FIG. 1) of the Velcro type. These tension adjusting members 58 and 60 are made of any elastic material similar to that used for the central section 12 and the cross-structure 26. These tension adjusting members 58 and 60 may be elongated only along their longitudinal axes Y, and each have a percent elongation ranging between 75 and 300. Each one of the tension adjusting members 58 and 60 is positioned generally parallel to its adjacent belt segment to which it is connected when the belt is worn by the user. The user stretches these tension adjusting members 58 and 60 to the desired length to achieve a comfortable belt tension around the pelvic region and establish stability. These tension adjusting members 58 and 60 are then secured in the elongated position by placing the hook sections 62 of the tensioning members in contact with the pile members 48 and 50, respectively, and pressing the hook sections into the pile members. The tension applied to the pelvic region of user can be increased or decreased as desired by simply repositioning the tension adjusting members 58 and 60.

To use the chiropractic belt 10 of this invention, the user simply opens the belt by pulling the hook member 54 from the pile member 48 and places the belt around his or her pelvic region as illustrated in FIGS. 7 and 8. To control the tension applied to the lower back portion, the user simply adjusts the tension applied by the tensioning members 58 and 60. For example, with the right hand, the user pulls the hook member 54 from the pile section 48, stretches the right hand tension adjusting member 60 lengthwise, and then pushes the hook member 54 back into the pile section 48 to hold the tension adjusting member 60 in an elongated condition. Then with the left hand, the user repeats the operation for the left hand tension adjusting member 58.

Figure 11:
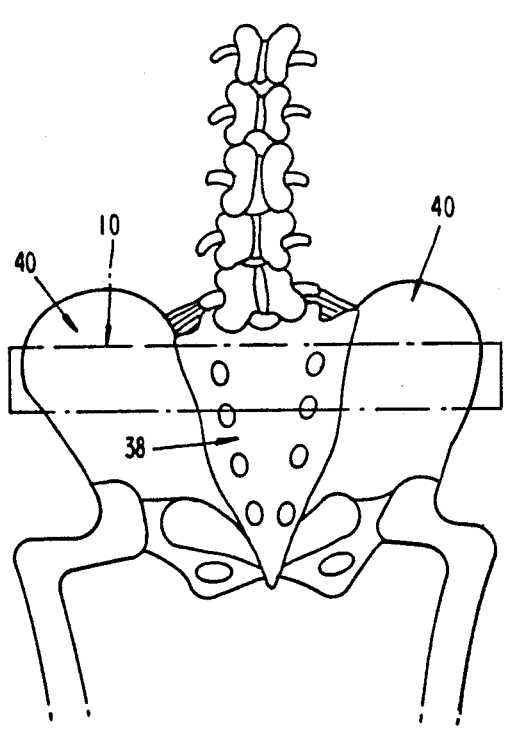
FIG. 11 is a schematic view of a human skeleton showing the position of chiropractic belt of this invention for correctly aligning sacrum and ilium.
Figure 10:
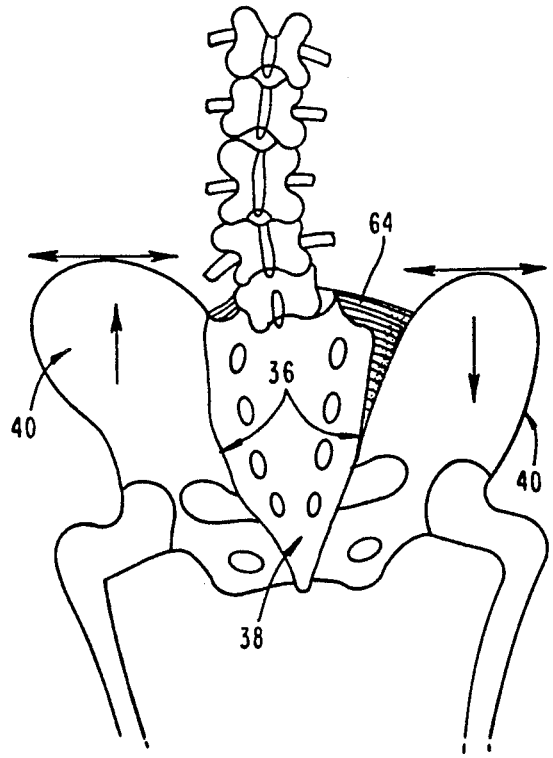
FIG. 10 is a schematic view of a human skeleton showing the sacrum and ilium misaligned.
Figure 12:
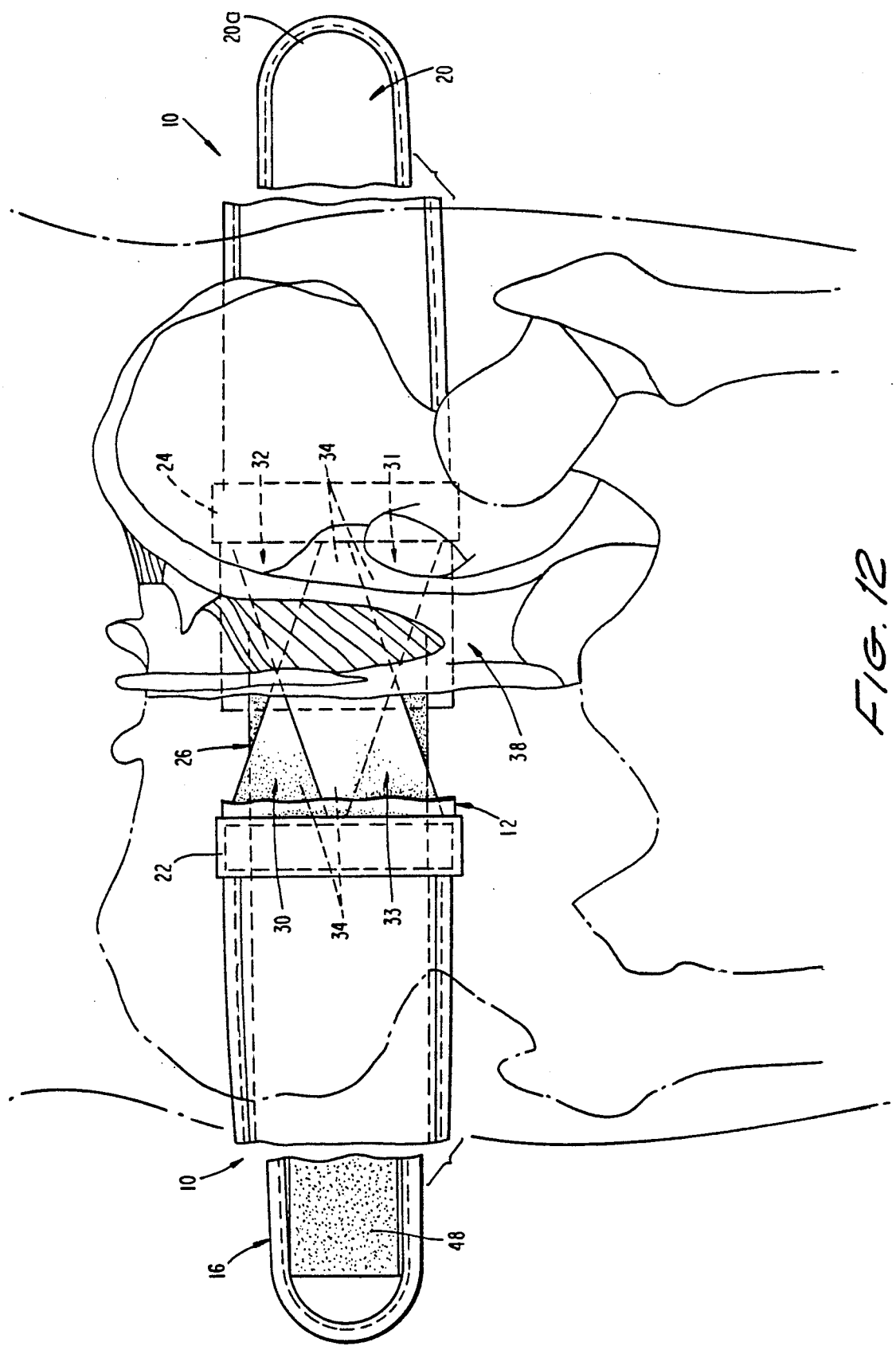
FIG. 12 is a schematic view of the posterior of a human skeleton showing the position of the central section of chiropractic belt of this invention relative to sacrum and ilium, with the user standing in an erect vertical stance.

As best illustrated in FIGS. 12 and 13, with the belt 10 correctly positioned about the pelvic region of the user as shown in FIG. 11, the pair of arms 30 and 31 are in tandem alignment with each other, with the upper arm 30 being substantially in parallel alignment with the left hand posterior sacro-iliac ligaments (not shown), and the pair of arms 32 and 33 are in tandem alignment with each other, with the upper arm 32 being substantially in parallel alignment with the right hand posterior sacro-iliac ligaments 64. If, for example, the right hand posterior sacro-iliac ligaments are strained as shown in FIG. 10, the belt corrects this condition over time. The arms 30 and 32 provide supplementary support for the sacrum 38 and ilium 40, tending to pull these bones together, enhancing the function of the posterior sacro-iliac ligaments. This relieves the tension in the ligaments, allowing the ligaments to shorten and stabilize, returning to their normal, unstrained condition. Moreover, these arms 30 and 32, as illustrated in FIG. 13, tend to stretch with movement generally in the same direction as the posterior sacro-iliac ligaments. This allows for freedom of movement to avoid atrophy. Central elastic section 12 tends to push inwardly against the lower back portion of the pelvis, again relieving pressure, strain, or both, on the posterior sacro-iliac ligaments. The design of the belt 10 allows for a free and full range of movement of the pelvic region. Consequently, the muscles are exercised by doing normal work and play, and therefore, do not atrophy. Yet the posterior sacro-iliac ligaments are not unduly strained so that they heal, reestablishing stability.

Although the above discussion assumes that the posterior sacro-iliac ligaments or other connecting tissue have been injured, the belt 10 could also be used as a preventative device to give additional support to the pelvic region so that the ligaments are not strained or sprained. For example, the belt 10 could be used during exercise, prolonged sitting, stooping, bending, or while engaged in sports such as golf, tennis, or bowling. One could sleep with the belt 10 on, if so desired, and could engage in all normal activities such as walking, sitting, standing, et cetera.

SCOPE OF THE INVENTION

The above description discloses the best mode contemplated of carrying out the present invention. This invention is, however, susceptible to modifications in the belt construction discussed above. Consequently, it is not the intention to limit this invention to the particular embodiments disclosed. On the contrary, the intention is to cover all modifications and alternatives coming within the spirit and scope of the invention as generally expressed by the following claims;

I claim:

1. A chiropractic belt comprising
   a first, flexible elastic member having opposed ends,
   a pair of flexible belt segments, each belt segment having a free end and another end attached to one of the opposed ends of the elastic member,
   fastener means on the belt segments which allow the free ends of the belt segments to be connected and disconnected,
   second and third flexible elastic members overlying the first elastic member and criss-crossing each other to intersect near the mid-section of the first elastic member,
   means for securing the second and third elastic members to each other and means for securing the first elastic member at the intersection of said second and third elastic members,
   fourth and fifth elastic members, each having one end secured at the intersection of the second and third elastic members, and each having a free end, each of said fourth and fifth elastic members extending outwardly from the intersection and being adapted to be aligned in parallel, overlying relationship with an adjacent belt segment, and
   means which allow the fourth and fifth elastic members to be connected and disconnected to their respective adjacent belt segments.

2. The chiropractic belt of claim 1 wherein the belt segments include an internal foam material.

3. The chiropractic belt of claim 1 wherein the connecting and disconnecting means are of the loop and pile type.

4. The chiropractic belt of claim 1 wherein the second and third flexible elastic members have a width of approximately two inches and an elongation ranging between 75 and 300 percent.

5. The chiropractic belt of claim 1 wherein the first flexible elastic member has a width ranging between four and one-half and five and one-half inches and a height ranging between three and one-half and four and one-half inches and a percent elongation along its longitudinal axis ranging between 75 and 300 percent and an essentially 0% elongation along its latitudinal axis.

6. A chiropractic belt worn around the pelvic region of a user, comprising
   a central elastic member having a midsection which generally overlies the sacroiliac region of a user when the belt is positioned correctly on the body of the user,
   said central elastic member having a left hand side with a left hand belt segment connected thereto and extending outwardly therefrom, and a right hand side with a right hand belt segment connected thereto and extending outwardly therefrom,
   said left and right hand belt segments each having free ends with means that allow the free ends to be connected and disconnected for securing the belt around the body of the patient in the vicinity of the pelvic region,
   a cross structure overlying the central elastic member having four flexible elastic arms, each arm having one end secured to and extending outwardly from the midsection of the central elastic member, and another end secured to an adjacent belt segment, and
   with the belt correctly positioned around the pelvic region of the user,
   a first pair of said arms being in tandem alignment with each other with one arm of said first pair being above the other arm of said first pair and generally in parallel alignment with the right hand posterior sacro iliac ligaments connecting the sacrum and the ilium of the user, and
   a second pair of said arms being in tandem alignment with each other with one arm of said second pair being above the other arm of said second pair and generally in parallel alignment with the left hand posterior sacro-iliac ligaments connecting the sacrum and the ilium of the user, and
   tensioning means for controlling the tension applied to the body of the user when the belt is properly positioned around the pelvic region of the user, said tensioning means including a right hand elastic tensioning member that has one end connected to the midsection of the central elastic member and a free end which can be connected or disconnected to the right hand belt segment and a left hand elastic tensioning member having one end connected to the midsection of the central elastic member and a free end which can be connected or disconnected to the left hand belt segment.

7. A chiropractic belt comprising a flexible elastic member having opposed ends, a pair of flexible belt segments, each belt segment having a free end and another end attached to one of the opposed ends of the elastic member, fastener means on the belt segments which allow the free ends of the belt segments to be connected and disconnected, an elastic cross-structure overlying and attached to the elastic member, a pair of tensioning members, each having one end secured to the cross-structure, each having a free end, and each extending outwardly from the cross-structure and being adapted to be aligned in parallel, overlying relationship with an adjacent belt segment, said cross-structure having four flexible elastic arms, each arm having one end secured to and extending outwardly from the midsection of the central elastic member, and another end secured to an adjacent belt segment, and with the belt correctly positioned around the pelvic region of the user, a first pair of said arms being in tandem alignment with each other with one arm of said first pair being above the other arm of said pair and generally in parallel alignment with the right hand posterior sacro-iliac ligaments connecting the sacrum and the ilium of the user, and a second pair of said arms being in tandem alignment with each other with one arm of said second pair being above the other arm of said second pair and generally in parallel alignment with the left hand posterior sacro-iliac ligaments connecting the sacrum and the ilium of the user, and means which allow the tensioning members to be connected and disconnected to their respective adjacent belt segments.

* * * * *